(12) United States Patent
Maher et al.

(10) Patent No.: US 8,382,830 B2
(45) Date of Patent: Feb. 26, 2013

(54) IMPLANTABLE VAD WITH REPLACEABLE PERCUTANEOUS CABLE

(75) Inventors: Tim Maher, Woods Cross, UT (US); Jim Lee, Benicia, CA (US); Ron Ness, Lincoln, CA (US); Herb Chen, Oakland, CA (US); Jesse Hubbard, Riverton, UT (US); Phillip J. Miller, Berkeley, CA (US); John Barr, Brea, CA (US); James W. Long, Salt Lake City, UT (US); Karl Nelson, Draper, UT (US)

(73) Assignee: World Heart Corporation, Salt Lake City, UT (US)

( * ) Notice: Subject to any disclaimer, the term of this patent is extended or adjusted under 35 U.S.C. 154(b) by 358 days.

(21) Appl. No.: 12/602,926

(22) PCT Filed: Jun. 6, 2008

(86) PCT No.: PCT/US2008/066137
§ 371 (c)(1),
(2), (4) Date: May 24, 2010

(87) PCT Pub. No.: WO2008/154393
PCT Pub. Date: Dec. 18, 2008

(65) Prior Publication Data
US 2010/0256440 A1 Oct. 7, 2010

Related U.S. Application Data

(60) Provisional application No. 60/933,606, filed on Jun. 6, 2007.

(51) Int. Cl.
*A61M 1/10* (2006.01)
(52) U.S. Cl. .......................... 623/3.1; 600/16
(58) Field of Classification Search ............... 600/16–18; 623/3.1, 3.27
See application file for complete search history.

(56) References Cited

U.S. PATENT DOCUMENTS

| | | | |
|---|---|---|---|
| 5,833,655 A | 11/1998 | Freed et al. | |
| 5,904,646 A | 5/1999 | Jarvik | |
| 6,305,962 B1 | 10/2001 | Maher et al. | |
| 6,709,382 B1 | 3/2004 | Horner | |
| 6,758,841 B2 * | 7/2004 | Haarala et al. | 604/513 |
| 2003/0120327 A1 | 6/2003 | Tobritzhofer et al. | |
| 2006/0030918 A1 | 2/2006 | Chinn et al. | |
| 2006/0036127 A1 | 2/2006 | Delgado | |
| 2006/0224110 A1 | 10/2006 | Scott et al. | |
| 2007/0038263 A1 | 2/2007 | McIntyre | |

OTHER PUBLICATIONS

International Preliminary Report on Patentability mailed Dec. 17, 2009 for application No. PCT/US2008/066137.

* cited by examiner

*Primary Examiner* — Brian T Gedeon
(74) *Attorney, Agent, or Firm* — Holland & Hart LLP

(57) ABSTRACT

There are disclosed apparatus and methods for replacing a percutaneous cable in connection with a vascular device. In an embodiment, the apparatus includes a distal disconnect coupler, a distal connector portion of the cable configured for removable connection with the distal disconnect coupler, and a connector cap configured for removable connection with the distal disconnect coupler and for tunneling through skin and tissue. In one embodiment, a method of repositioning a percutaneous cable in connection with a vascular device includes providing the cable with a distal disconnect coupler, disconnecting the cable at the distal disconnect coupler, attaching a connector cap to the distal disconnect coupler, removing the percutaneous cable from a first exit site, tunneling the connector cap together with the distal disconnect coupler through skin and tissue to form a new exit site, disconnecting the connector cap, and connecting the cable to the distal disconnect coupler.

18 Claims, 9 Drawing Sheets

IMPLANTABLE VAD WITH REPLACEABLE PERCUTANEOUS CABLE

REFERENCE TO PENDING PRIOR PATENT APPLICATION

This application claims the benefit under 35 U.S.C. 119 (e) of U.S. Provisional Patent Application No. 60/933,606, filed Jun. 6, 2007 by Tim Maher, et al. for "IMPLANTABLE VAD WITH REPLACEABLE PERCUTANEOUS CABLE," which patent application is hereby incorporated herein by reference.

BACKGROUND

Ventricular assist devices ("VAD") pump blood in parallel with the native ventricles of the human heart. This provides blood flow to the body when the patient's own heart is in failure. A typical implantation of a VAD in the left side configuration takes blood from the apex of the left ventricle and returns blood to the ascending aorta at higher pressure. The VAD thereby takes on a significant portion of the work done by the native heart without removing the native heart.

VADs are at times used in temporary applications, such as bridge to heart transplantation or bridge to recovery of the native heart. However, the largest application of VAD's is likely to be long-term use of the device through the duration of the patient's life. This is also known as destination therapy ("DT") use of the device.

SUMMARY OF THE INVENTION

In an embodiment, there is provided an apparatus for replacing a percutaneous cable in connection with a vascular device, the apparatus comprising a distal disconnect coupler in the percutaneous cable at a distal location from the vascular device; a distal connector portion at the distal location of the percutaneous cable, the distal connector portion configured for removable connection with the distal disconnect coupler so as to allow replacement of at least a portion of the percutaneous cable; and a connector cap configured for removable connection with the distal connector portion, the connector cap configured for tunneling through skin and tissue; wherein the connector cap is configured for attachment to the distal connector portion when the percutaneous cable is positioned through an exit site of a patient, and the connector cap is configured for removal from the distal connector portion when the percutaneous cable is positioned through the exit site of a patient and prior to attachment of the distal disconnect coupler and the distal connector portion to one another.

In another embodiment, there is provided an apparatus for replacing a percutaneous cable in connection with a vascular device, the apparatus comprising a proximal disconnect coupler in the percutaneous cable at a proximal location to the vascular device; and a proximal connector portion at the proximal location of the percutaneous cable, the proximal disconnect coupler having a relatively flat form factor, and the proximal connector portion configured for removable connection with the proximal disconnect coupler so as to allow replacement of at least a portion of the percutaneous cable.

In yet another embodiment, there is provided an apparatus for replacing a percutaneous cable in connection with a vascular device, the apparatus comprising a proximal disconnect coupler in the percutaneous cable at a proximal location to the vascular device; and a proximal connector portion at the proximal location of the percutaneous cable, the proximal disconnect coupler having a set of connections in a linear relationship to one another, and the proximal connector portion configured for removable connection with the proximal disconnect coupler so as to allow replacement of at least a portion of the percutaneous cable.

In still another embodiment, there is provided a method of repositioning a percutaneous cable in connection with a vascular device, the method comprising providing the percutaneous cable with a distal disconnect coupler at a distal location from the vascular device at a location outside of an exit site of the percutaneous cable; disconnecting a distal connector portion of the percutaneous cable at the distal disconnect coupler; subsequent to disconnecting the percutaneous cable, attaching a connector cap to the distal connector portion; subsequent to disconnecting the percutaneous cable, removing the percutaneous cable from a first exit site; subsequent to attaching the connector cap, tunneling the connector cap together with the distal connector portion of the percutaneous cable through skin and tissue to form a new exit site; disconnecting the connector cap from the distal connector portion; and connecting the percutaneous cable to the distal disconnect coupler.

In still another embodiment, there is provided a method of positioning a percutaneous cable relative to a vascular device, the method comprising providing the percutaneous cable with a proximal disconnect coupler at a proximal location from the vascular device; providing the vascular device with a rotatable connection between a motor capsule and a housing; and rotating the motor capsule and the housing to position the percutaneous cable relative to the vascular device.

Other embodiments also are disclosed.

BRIEF DESCRIPTION OF THE DRAWINGS

Illustrative embodiments of the invention are illustrated in the drawings, in which.

DETAILED DESCRIPTION

Figure 1:
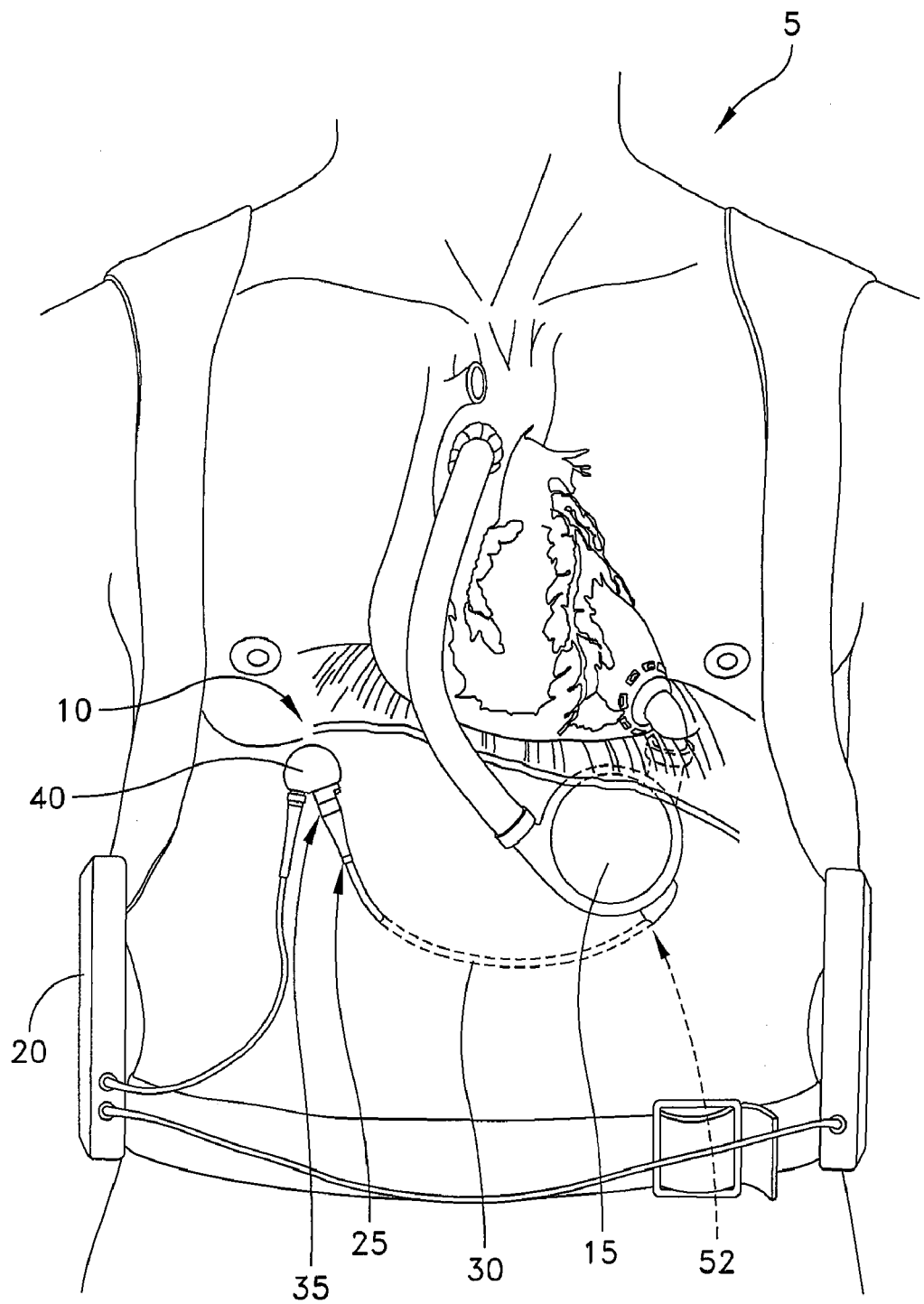
FIG. 1 illustrates one exemplary embodiment of an implantable VAD with a replaceable percutaneous cable.

In various exemplary embodiments, there are provided methods and apparatus of managing the care of long-term VAD patients, also known as DT VAD patients. Generally, the embodiments illustrate partial and full replacement of the percutaneous cable.

The embodiments generally relate to vascular devices, including implantable VADs. More particularly, these vascular devices include a cable that goes from outside the body to inside the body, also known as a percutaneous cable.

Electric VADs require some external source of power, such as a battery when the patient is mobile, or connection to the AC mains power when the patient is sleeping or otherwise stationary. Typically, an electronic controller is required to control the pumping apparatus, and to modulate the delivery of the external power to the pumping apparatus. Such an electronic controller may be either outside of, or inside of, the body. In either case, a percutaneous cable passes through the skin and surrounding tissue, to deliver power and/or control and communication signals to the internal pumping apparatus.

One of the primary goals in the clinical treatment of ventricular assist patients is to have them return to everyday activities after recovery from the implantation procedure as soon as possible. In the course of these everyday activities, the external part of the percutaneous cable is subjected to wear and tear of motion of the person, accidental cuts, or other general abuse that may cause the VAD to stop pumping long before other elements of the system wear out. As a result, providing that the distal portion of the cable (i.e., the portion of cable furthest from the pumping apparatus) be replaceable on an as-needed basis is a considerable improvement over the state of the art.

Such replacement may be done in response to damage done to the cable in a specific event, or may be done as a preventative step to avoid failure of the cable due to long-term general use.

During the course of everyday life of VAD patients with their device, the tissue and skin around the point where the cable exits the body can become traumatized or injured through accidental pulling on the cable or other events. Trauma to the exit site can result in infections and injury that are difficult to heal without replacing the cable and moving the new cable to a new site.

In addition, and in another embodiment, the proximal end of the cable (i.e. the end closest to the pumping apparatus) may be replaced without replacing other internal implantable components. It is believed to be a significant advance in the state of the art to provide a percutaneous cable configured to be fully replaceable without replacing the implantable pump.

It should be noted that other approaches to delivering power to VAD systems have been developed, such as transcutaneous energy transmission, that do not require percutaneous cables going through the skin. The embodiments disclosed herein require a percutaneous cable, such that these other approaches do not apply to VAD systems having percutaneous cables.

FIG. 1 shows an embodiment of a VAD system 5. In FIG. 1, there is shown an in-line connector 10 between a pump 15 and a controller 20 just outside the skin. The in-line connector 10 is designed to be low and flat in profile to allow the patient to place it against the skin using adhesive tape or other methods. The in-line connector 10 in the position shown allows for replacement of the distal end 25 of the percutaneous cable 30 with disturbing any of the implantable elements of the VAD system 5.

Figure 2:
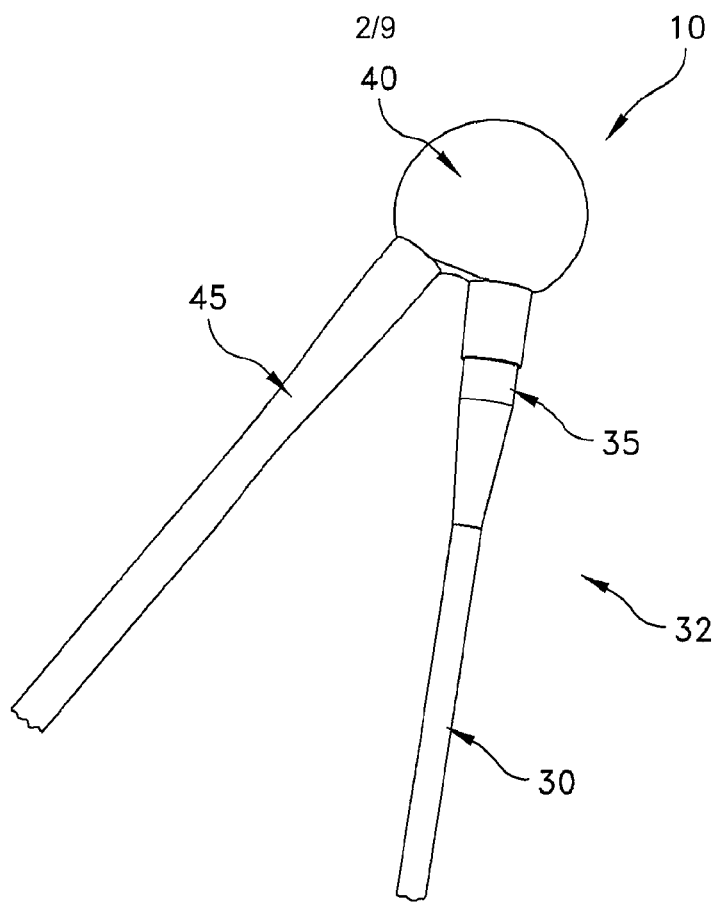
FIG. 2 is a view of the percutaneous cable in-line connector shown in FIG. 1.

As shown in FIG. 2, the pump side 32 of the in-line connector 10 has a "tunneled connector" 35 that disconnects from the in-line connector body 40 on the pumpside 32. The in-line connector body 10 on the opposite side may connect with cable 45 leading to controller 20. The pumpside 32 designed to be passed through the skin at the time of surgery. The connections may sometimes be referred to by their location and the like. For example, the connector may be referred to as a distal disconnect coupler and the distal end of the percutaneous cable may be referred to as the distal connector portion and cable portions. The same may be said for the connector proximal the VAD.

Figure 2A:
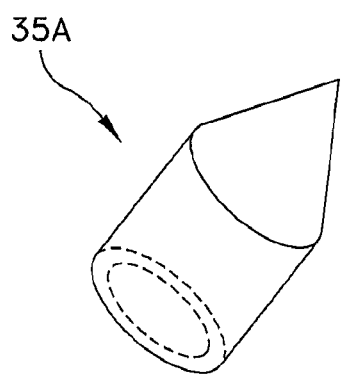
FIG. 2A illustrates a connector cap for use with the percutaneous cable of FIG. 1.

In an embodiment, a small diameter of tunneled connector 35 may be provided to minimize the exit site wound size, and mechanical design features may be provided for firm attachment of a connector cap 35A (FIG. 2A) to facilitate tunneling of the connector 35 through the skin and tissue. Such mechanical design features may include threads, twist locks, mechanical compression lock or other methods to reliably fix a tunneling cap to the connector 35.

Figure 3:
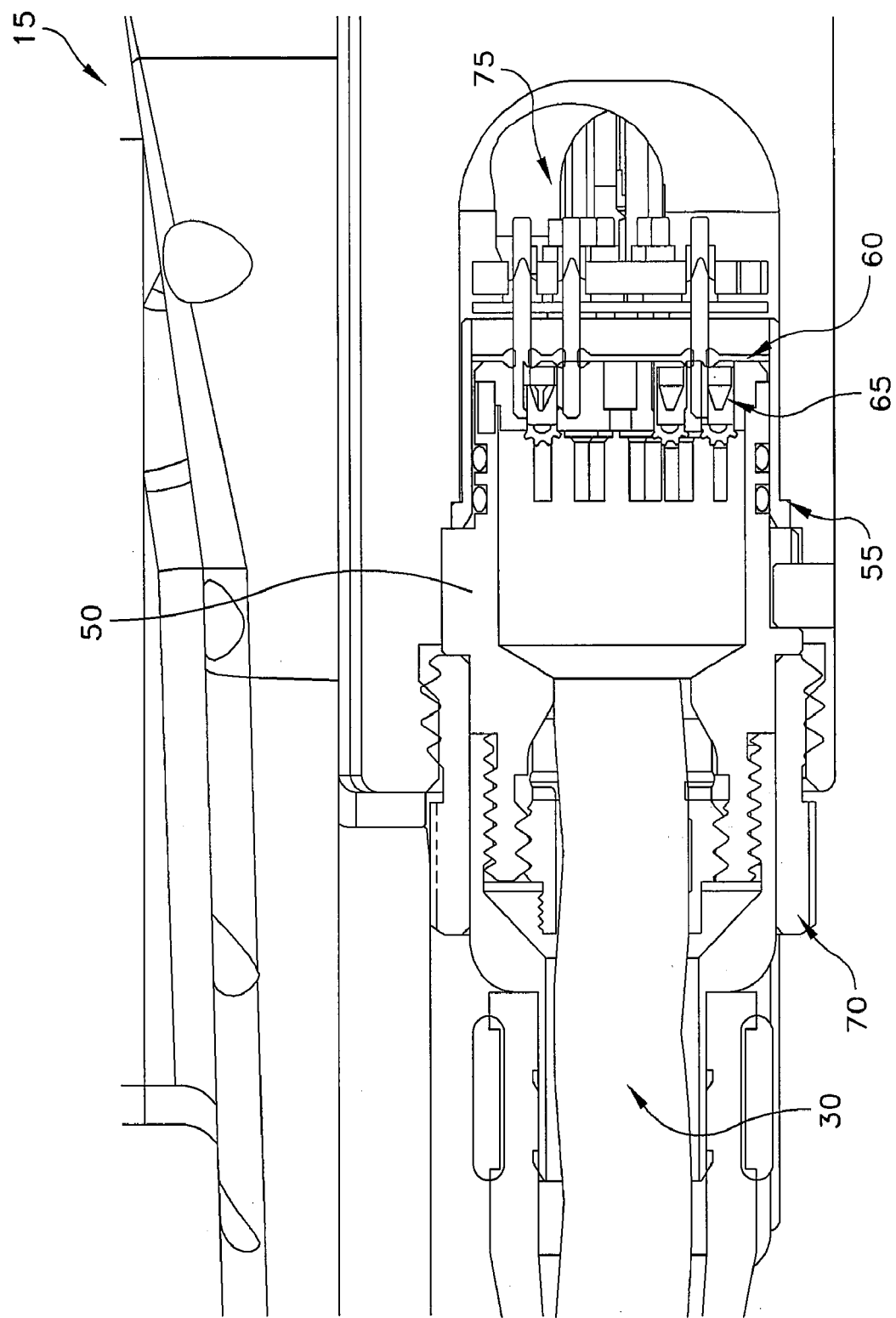
FIG. 3 is a view of the implantable percutaneous cable connector.

FIG. 3 shows a view of an implantable connector 50 that allows a proximal end 52 (FIG. 1) of percutaneous cable 30 to be replaced from pump 15 to the tunneled connector 35. The implantable connector 50 is designed to minimize the bulk of the connector 50 and still allow complete replacement of the cable 30. Design features include redundant seals 55, 60 to keep the connector contacts 65 free from fluids throughout the life of the implanted device. A screw-on retaining ring 70 also may be provided for attaching cable 30 and connector 50 to one another. A hermetically sealed chamber 75 also may be formed within pump 15.

U.S. Pat. No. 5,833,655, issued to Freed et al., discloses a percutaneous access device having a removable turret assembly. Freed et al. disclose a mechanical structure that has a turret protruding outside the skin that can be replaced without disturbing the implanted portion of the assembly. Such an approach is significantly different than moving a cable exit site to a new location in the event of infection at the original site.

It should be appreciated by those skilled in the art and the clinical use of implantable mechanical circulatory support devices that the ability to replace the distal end 25 of VAD percutaneous cable 30 would be an improvement to existing devices. It should further be appreciated by those skilled in the art that the ability to replace the entire percutaneous cable 30 with surgery that does not require pump replacement is an improvement over existing devices.

It also should be appreciated by those skilled in the art that apparatus and methods apply equally to many types of mechanical circulatory support devices, in addition to VADs, including, but not limited to, 1) left ventricular assist devices, 2) right ventricular assist devices, 3) total artificial hearts (when the native heart is removed), 4) mechanical assist blood pumps that are placed in areas of the circulatory system that do not directly assist the ventricles of the heart.

Figure 4:
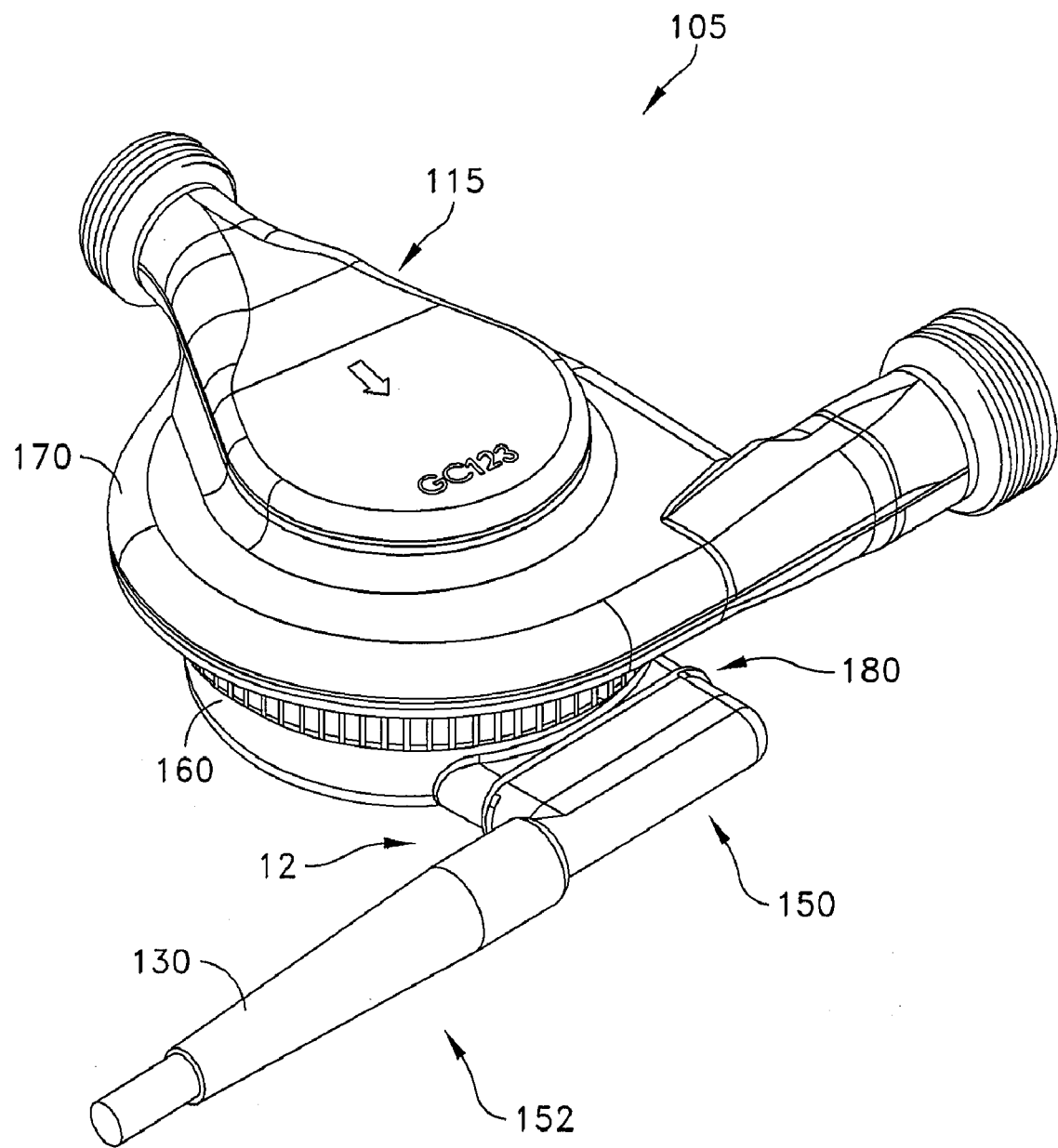
FIG. 4 illustrates another exemplary embodiment of an implantable VAD with a replaceable percutaneous cable.

Referring now to FIG. 4, and in another embodiment there is illustrated a pump 115 with a portion of a VAD system 105. An implantable connector 150 may be provided that allows a proximal end 152 of percutaneous cable 130 to be replaced from a pump 115 to external in-line connector (not shown). Implantable connector 150 may be a low profile connector to minimize the bulk of the connector 150 and still allow complete replacement of the cable 130. Connector 150 may include a series of pins 165 (FIG. 6) in a linear relationship to one another. The linear relationship of pins 165 allows a lower profile configuration than other tubular pin configurations.

Figure 5:
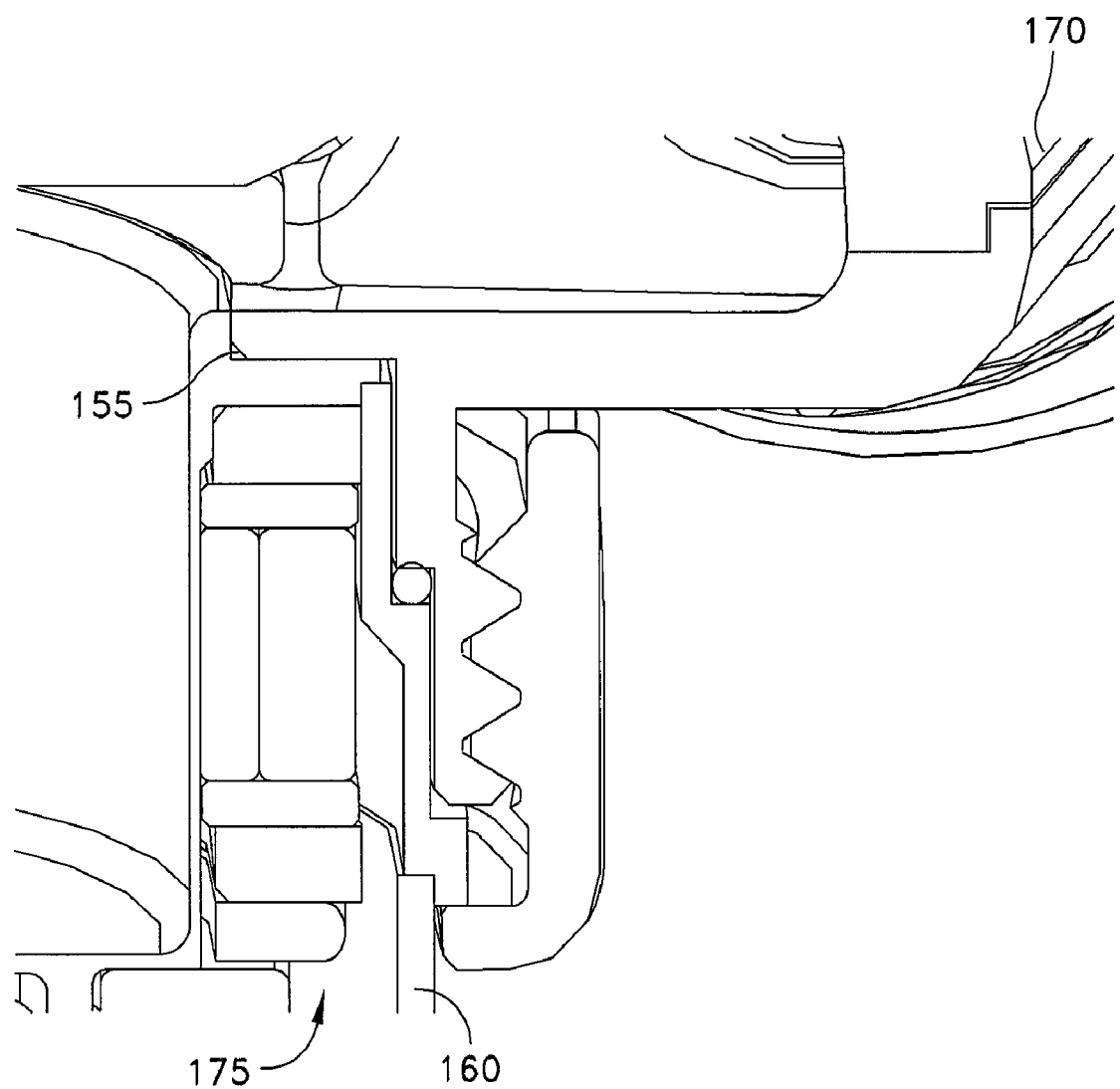
FIG. 5 illustrates a portion of the housing of the implantable VAD shown in FIG. 4.
Figure 8:
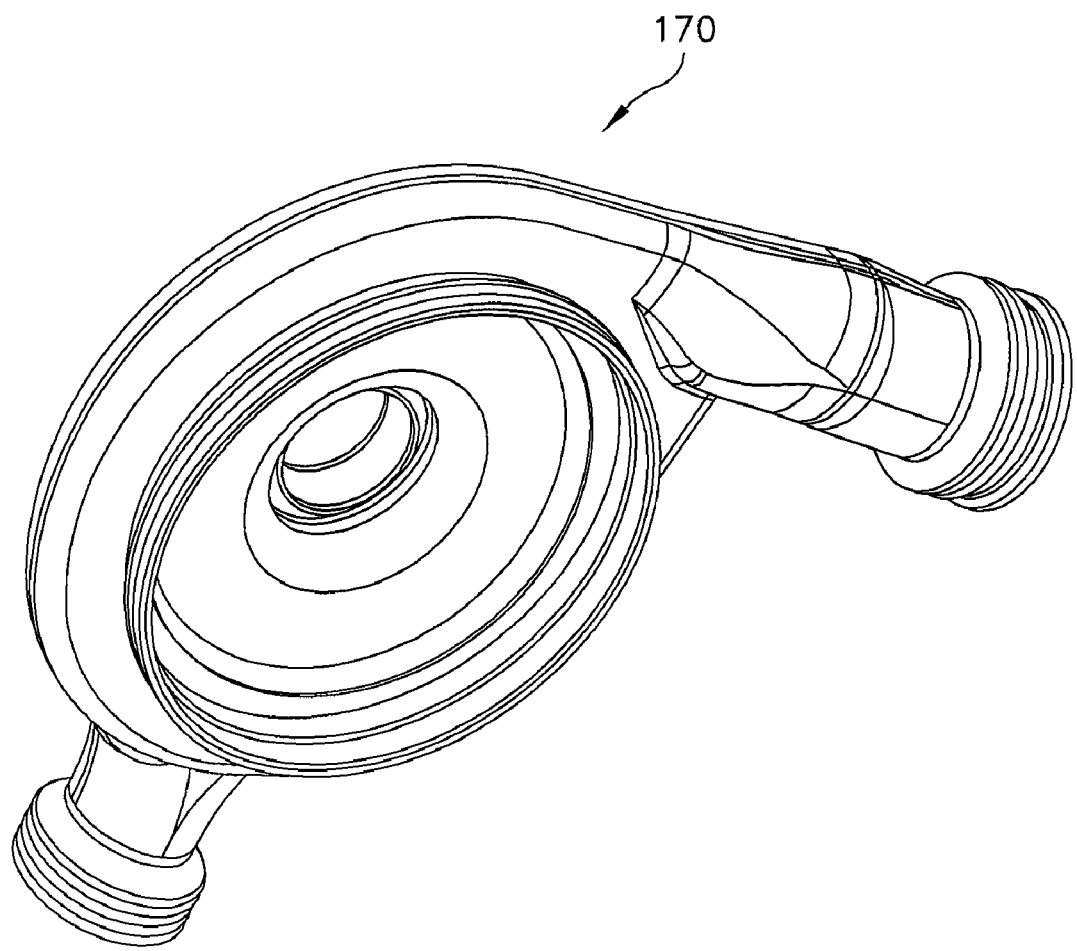
FIG. 8 illustrates an interior view of the housing of the implantable VAD shown in FIG. 4.
Figure 9:
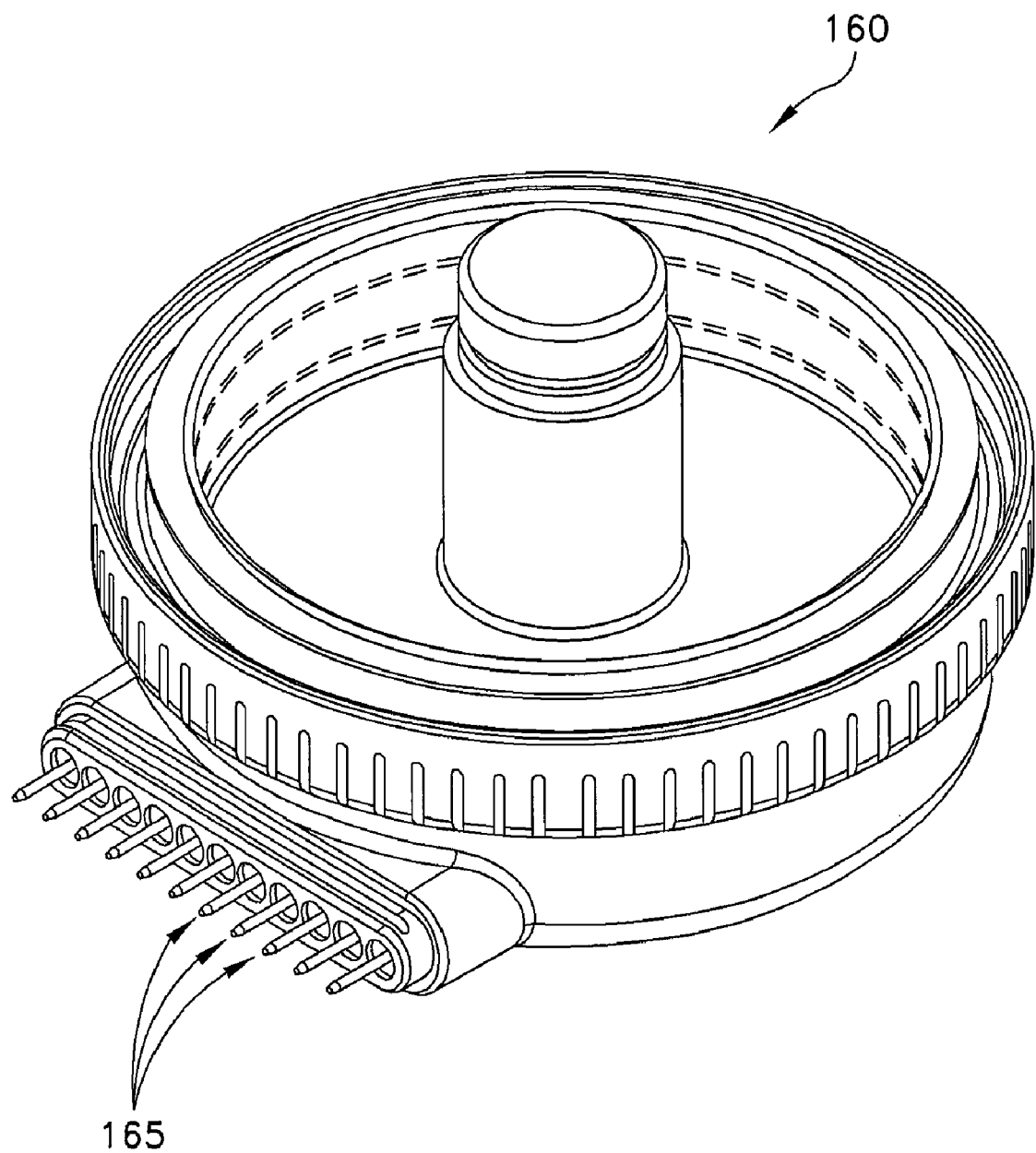
FIG. 9 illustrates an interior view of the hermetic motor capsule of the implantable VAD shown in FIG. 4.

Referring to FIG. 5, there is shown a set of pre-assembled magnets and coils 175 in housing 170. VAD system 105 may include one or more non-welded seam 155 so as to allow rotation of a hermetic motor capsule 160 (also shown in FIG. 9) relative to a housing 170 (also shown in FIG. 8.)

Figure 7A:
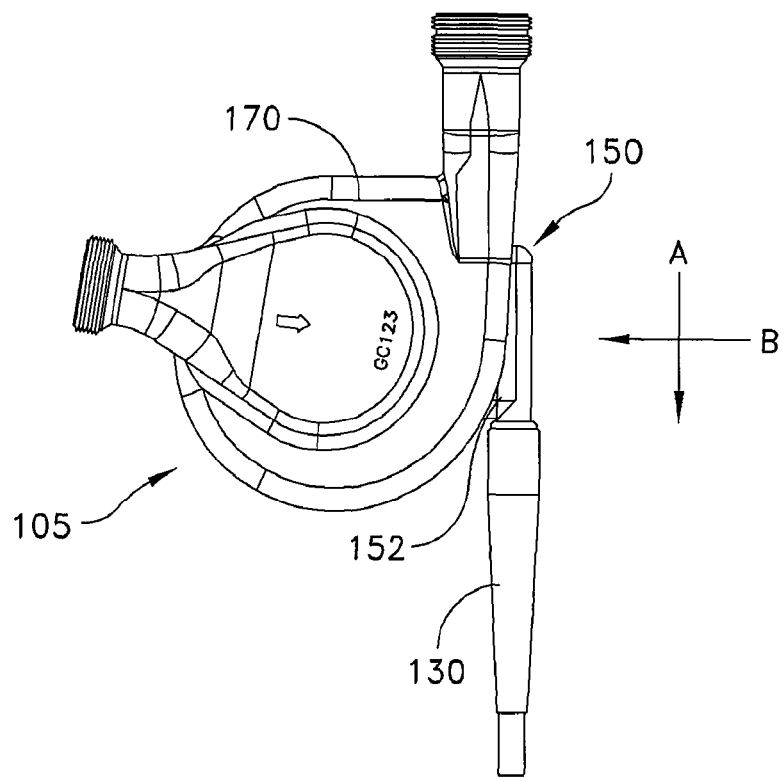
FIGS. 7A and 7B illustrate two different positions of the percutaneous cable and the housing of the implantable VAD shown in FIG. 4 relative to one another.
Figure 7B:
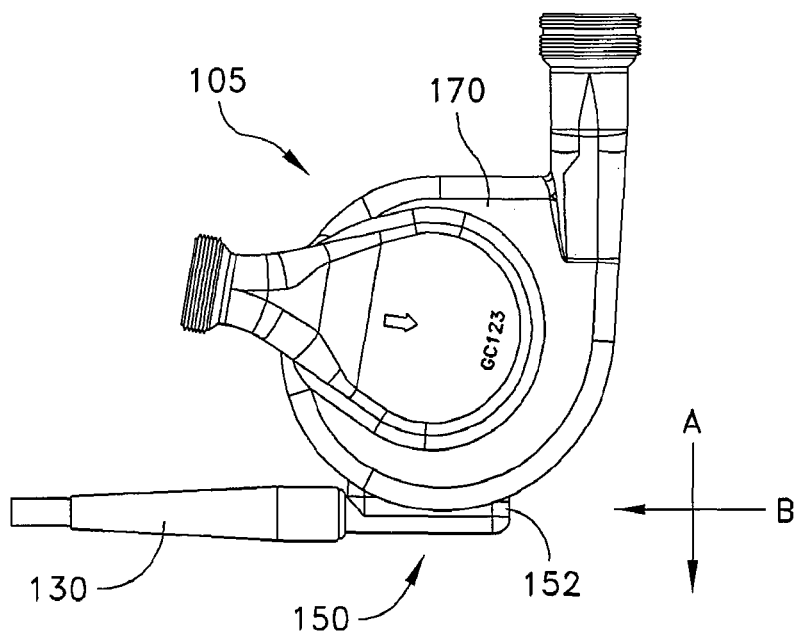

As best illustrated in FIGS. 7A and 7B, percutaneous cable 130 may be freely positionable with respect to housing 170 due to the non-welded seam 155. In FIG. 7A, cable 130 is located in a direction A away from housing 170. In FIG. 7B, cable 130 is located in a direction B away from housing 170.

Depending on the anatomy of the patient, the location of components of VAD system 105, and the location of the percutaneous exit of cable 130, rotation of hermetic motor capsule 160 may allow better positioning of these components or a shorter percutaneous cable 130.

Figure 6:
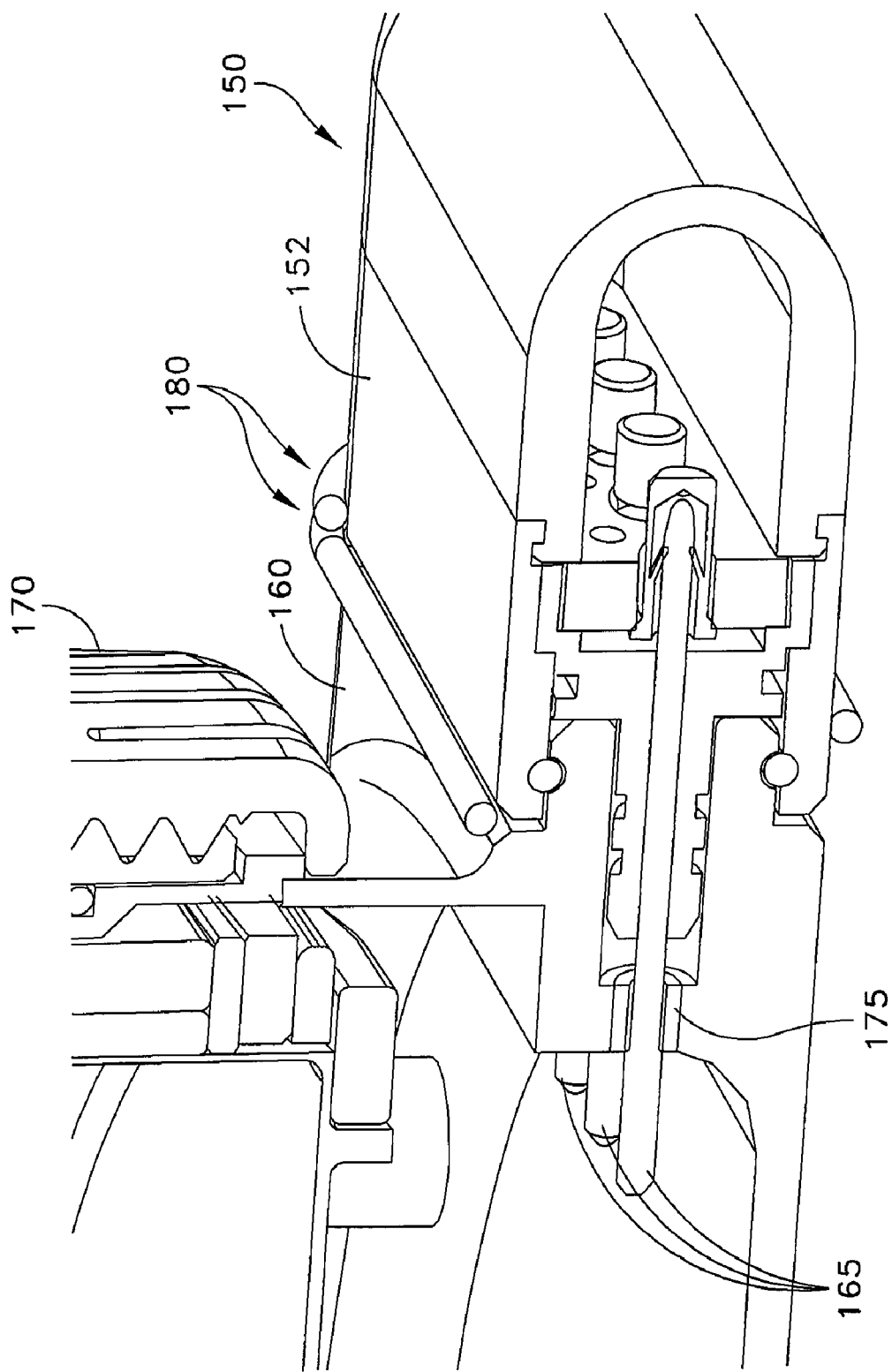
FIG. 6 illustrates a portion of a connection between the housing and the percutaneous cable of the implantable VAD shown in FIG. 4.

Looking at FIG. 6, an individual feed-through 175 may be provided through housing 170 for each of the pins 165. In addition, one or more o-rings 180 may be provided to seal connector 150 and housing 170 together with one another.

It should also be appreciated by those skilled in the art that apparatus and methods apply equally to many types of mechanical circulatory support devices, in addition to VADs, including, but not limited to, left ventricular assist devices, right ventricular assist devices, total artificial hearts (when the native heart is removed), mechanical assist blood pumps that are placed in areas of the circulatory system that do not directly assist the ventricles of the heart.

What is claimed is:

1. Apparatus for replacing a percutaneous cable in connection with a vascular device, the apparatus comprising:
   a distal disconnect coupler in the percutaneous cable at a distal location from the vascular device;
   a distal connector portion at the distal location of the percutaneous cable, the distal connector portion configured for removable connection with the distal disconnect coupler so as to allow replacement of at least a portion of the percutaneous cable; and
   a connector cap configured for removable connection with the distal connector portion, the connector cap configured for tunneling through skin and tissue;
   wherein the connector cap is configured for attachment to the distal connector portion when the percutaneous cable is positioned through an exit site of a patient, and the connector cap is configured for removal from the distal connector portion when the percutaneous cable is positioned through the exit site of a patient and prior to attachment of the distal disconnect coupler and the distal connector portion to one another.

2. Apparatus in accordance with claim 1, further comprising:
   a proximal disconnect coupler in the percutaneous cable at a proximal location to the vascular device; and
   a proximal connector portion at the proximal location of the percutaneous cable, the proximal connector portion configured for removable connection with the proximal disconnect coupler so as to allow replacement of at least a portion of the percutaneous cable.

3. Apparatus in accordance with claim 2, wherein the proximal disconnect coupler has a relatively flat form factor.

4. Apparatus in accordance with claim 2, wherein the proximal disconnect coupler has a set of connections in a linear relationship to one another.

5. Apparatus in accordance with claim 1, wherein the distal disconnect coupler is configured for positioning at a location outside of an exit site of the percutaneous cable.

6. Apparatus in accordance with claim 5, wherein the distal disconnect coupler is configured for placement adjacent the exit site and protection by a covering together with the percutaneous cable.

7. Apparatus in accordance with claim 6, wherein the distal disconnect coupler and the percutaneous cable are configured to be covered together with tape at the exit site.

8. Apparatus in accordance with claim 6, wherein the distal disconnect coupler and the percutaneous cable are configured to be covered together with a binder around the exit site.

9. A method of repositioning a percutaneous cable in connection with a vascular device, the method comprising:
   providing the percutaneous cable with a distal disconnect coupler at a distal location from the vascular device at a location outside of an exit site of the percutaneous cable;
   disconnecting a distal connector portion of the percutaneous cable at the distal disconnect coupler;
   subsequent to disconnecting the percutaneous cable, attaching a connector cap to the distal connector portion;
   subsequent to disconnecting the percutaneous cable, removing the percutaneous cable from a first exit site;
   subsequent to attaching the connector cap, tunneling the connector cap together with the distal connector portion of the percutaneous cable through skin and tissue to form a new exit site;
   disconnecting the connector cap from the distal connector portion while the distal connector portion remains in position through the skin and tissue at the new exit site; and
   connecting the percutaneous cable to the distal disconnect coupler while the distal connector portion remains in position through the skin and tissue at the new exit site.

10. A method in accordance with claim 9, further comprising:
    replacing a distal portion of the percutaneous cable with a replacement distal portion percutaneous cable by connecting the replacement distal portion percutaneous cable to the disconnect coupler.

11. A method in accordance with claim 9, further comprising:
    replacing a proximal portion of the percutaneous cable with a replacement proximal portion percutaneous cable by connecting the replacement proximal portion percutaneous cable to the disconnect coupler.

12. A method in accordance with claim 9, further comprising:
    placing the distal disconnect coupler adjacent the exit site; and
    protecting the distal disconnect coupler together with the percutaneous cable with a covering.

13. A method in accordance with claim 9, wherein the protecting the distal disconnect coupler together with the percutaneous cable with a covering includes using tape at the exit site.

14. A method in accordance with claim 9, wherein the protecting the distal disconnect coupler together with the percutaneous cable with a covering includes using a binder at the exit site.

15. A method in accordance with claim 9, further comprising:
    disconnecting the percutaneous cable from the vascular device; and
    replacing a proximal portion of the percutaneous cable with a replacement proximal portion percutaneous cable by connecting the replacement proximal portion percutaneous cable to the vascular device.

16. A method of positioning a percutaneous cable relative to a vascular device, the method comprising:
    providing the percutaneous cable with a proximal disconnect coupler at a proximal location from the vascular device;
    providing the vascular device with a rotatable connection between a motor capsule and a housing; and rotating the motor capsule relative to the housing to displace the proximal disconnect coupler from a first position relative to the housing to a second position relative to the housing.

17. A method in accordance with claim 16, further comprising:

attaching the proximal disconnect coupler of the percutaneous cable to the motor capsule prior to rotating the motor capsule and the housing.

18. A method in accordance with claim 16, further comprising:

disconnecting the percutaneous cable from vascular device; and replacing a proximal portion of the percutaneous cable with a replacement proximal portion percutaneous cable by connecting the replacement proximal portion percutaneous cable to the vascular device.

* * * * *